(12) United States Patent
Breviglieri et al.

(10) Patent No.: US 7,151,193 B2
(45) Date of Patent: Dec. 19, 2006

(54) PROCESS FOR THE PREPARATION OF PURE GABAPENTIN "FORM II"

(75) Inventors: Gabriele Breviglieri, Treviglio (IT); Sergio Contrini, Treviglio (IT); Cinzia Assanelli, Treviglio (IT)

(73) Assignee: Farchemia s.r.l., Treviglio (IT)

( * ) Notice: Subject to any disclaimer, the term of this patent is extended or adjusted under 35 U.S.C. 154(b) by 128 days.

(21) Appl. No.: 10/769,886

(22) Filed: Feb. 3, 2004

(65) Prior Publication Data
US 2004/0176639 A1    Sep. 9, 2004

(30) Foreign Application Priority Data
Feb. 4, 2003    (IT)    ............................ MI2003A0176

(51) Int. Cl.
*C07C 61/08*    (2006.01)

(52) U.S. Cl. .................................................... 562/507
(58) Field of Classification Search .................. 562/507
See application file for complete search history.

(56) References Cited

U.S. PATENT DOCUMENTS 6,255,526 B1 *    7/2001    Pesachovich et al. ....... 562/507

OTHER PUBLICATIONS

Grant et al , Chemcial Dictionary, 1987, p. 220.*

* cited by examiner

*Primary Examiner*—Taylor Victor Oh
(74) *Attorney, Agent, or Firm*—Young & Thompson

(57) ABSTRACT

Pure gabapentin form II can be directly obtained adding the solution of the corresponding hydrochloride in dry ethanol (from which the inorganic salts have been filtered off) with a tertiary amine and a small amount of water.

19 Claims, No Drawings

PROCESS FOR THE PREPARATION OF PURE GABAPENTIN "FORM II"

The present invention relates to a process for the preparation of highly pure gabapentin base crystalline form II, starting from crude gabapentin hydrochloride.

TECHNOLOGICAL BACKGROUND

"Gabapentin" is the non-proprietary name of 1-(aminomethyl)-cyclohexaneacetic acid, a known medicament for the treatment of cerebral disorders, of formula

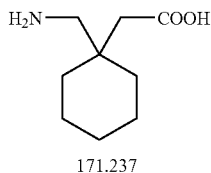

171.237

A number of processes for the preparation and/or the purification of gabapentin are known: see, for example, U.S. Pat. Nos. 4,024,175; 5,068,413; 5,091,567; 5,132,451; 5,319,135; 5,362,883; 6,054,482. More recently, WO 98/28255 disclosed and claimed a "process for converting gabapentin hydrochloride substantially free of inorganic salts to gabapentin form II", i.e. the commercially available form, characterized by an X-ray diffraction pattern with peaks of 2-theta values at 7.8, 13.3, 15.0. 17.0. 20.4, 21.3, 23.1, 23.6, 25.7, 27.0 and 28.2 degrees. Although the claims of said application are in part ambiguous, the disclosure and the examples clearly show that the process involves the following steps:

a) preparation of the hydrochloride free of inorganic salts by dissolution in a solvent (isopropanol, ethyl acetate and the like) in which said salts are not soluble, filtration of the salts and b) concentration of the filtrate to dryness;

c) dissolution of the resulting hydrochloride in a "first solvent" and addition of an amine (tributylamine in almost all of the examples), with precipitation and recovery of a gabapentin crystalline form referred to as "form III", which is different from form II, as shown by the X-ray diffraction pattern;

d) digestion of gabapentin form III in a "second solvent" (isopropanol in most examples) at comparatively low temperatures, for some hours, and/or crystallization from said solvent, thus obtaining the desired form II;

e) final purification through recrystallization (from methanol).

WO 98/28255 claims ethyl acetate, dimethylcarbonate, ethanol, butanol, t-butanol, n-butanol, methanol, acetonitrile, toluene, isopropyl acetate, isopropanol, methyl ethyl ketone, acetone, ethylene glycol monomethyl ether, methylene chloride, chloroform, benzyl alcohol or dimethylacetamide, in particular ethyl acetate, as the "first solvent"; triethylamine, tributylamine, tripropylamine, trihexylamine, diethylamine, ethanolamine and benzylamine, particularly tributylamine, as the amine to be added to the gabapentin hydrochloride solution; and finally methanol, ethanol, n-propanol, isopropanol, butanol, t-butanol, n-butanol, ethylene glycol monomethyl ether, benzyl alcohol or dimethylacetamide, particularly isopropanol, as the "second solvent" according to claim 12 and most examples.

Of the eleven examples 1-2-3-4-5-7-8-9-10-15-16 which indicate that the form II is subjected to treatments a)-b)-c)-d)-e), the overall yield is 66.4% on the average.

THE PROCESS ACCORDING TO THE INVENTION

It has now surprisingly been found that gabapentin hydrochloride can be used as the starting material for the preparation of the pure form II of the corresponding base in a remarkably simpler manner than the above mentioned one, with a notable saving of time, apparatuses and labour, by dissolving gabapentin hydrochloride in dry ethanol and filtering off the insoluble inorganic salts, then adding the filtered solution with tertiary amines, preferably the so-called "Hünig base" (N-ethyl-diisopropylamine), and a small amount of water. Upon simple cooling of the resulting solution and seeding with gabapentin form II, the desired polymorph (form II) precipitates in an already remarkably pure form, i.e. i) with a content in the corresponding lactam lower than 0.1% by weight, and ii) with a content in Cl⁻ ions not higher than 200–250 parts per million, which content can be reduced below 100 parts per million by trituration in ethanol, addition of water approx. 8–12% by volume, and cold filtration.

According to the invention, the weight/volume ratio of gabapentin hydrochloride to dry ethanol ranges from 1:6 to 1:9, preferably from 1:6.5 to 1:8. The solution resulting from filtration of the inorganic salts is added with 1 to 1.25 mols, preferably 1.1 to 1.2 mols, of tertiary amine, particularly N-ethyldiisopropylamine, and with an amount of water ranging from 7 to 10% by volume, preferably from 8 to 9.5%, by volume.

The resulting mixture is cooled to approx. 10–20° C., preferably to approx. 15° C., and seeded with a small amount of gabapentin form II. The mixture is kept at this temperature for some hours (4–8), cooled to −5 to +5° C., preferably 0° C., filtered, washed with dry ethanol precooled at 0° C. and dried. The precipitate, consisting of the polymorph II, contains not more than 0.1% by weight of the corresponding lactam and 200–250 parts per million of Cl⁻ ions on average. As already mentioned, the chloride ions content can be reduced below 100 ppm by treatment with approx. 10 parts by volume of ethanol added with approx. 10% by volume of water; the resulting slurry is kept at 35–45° C. for 10–15 minutes and left at room temperature overnight, after that the purified gabapentin form II is recovered by filtration or centrifugation with a 75% average yield, starting from the hydrochloride. A further, remarkable advantage of the process of the invention is that the operations are very easy: said yield is, as already mentioned, obtained without recovering gabapentin hydrochloride free of salts and without the step through the "form III".

EXAMPLE 1

1 kg (3.46 mols) of gabapentin hydrochloride (prepared by Hoffmann degradation of 1,1-ciclohexanediacetic acid monoamide according to DE 2,460,891) is suspended in 7 liters of dry ethanol; the mixture is heated to 40–45° C. for about 30 minutes under stirring, insolubles (NaCl) centrifuged off, and the precipitate is washed with 400–500 ml of dry ethanol. The filtrate is added with 522 g (4.04 mols) of N-ethyl-diisopropylamine and 660 ml of water; the mixture is cooled to 15–20° C., seeded with a few grams of gabapentin form II, left at this temperature for some hours, cooled to 0° C., then after one hour is centrifuged and the precipitate is washed with 800 ml of cool dry ethanol. 530 g of gabapentin form II, containing about 400 ppm of NaCl, are obtained; yield 89.4%.

The product is triturated in about 500 ml of ethanol containing 10% of water, heated for some minutes at 40° C., left to stand at room temperature for some hours, then at 0° C. for two hours and centrifuged to decrease the NaCl content below of 100 ppm, whereas the lactam content is below 0.1%. The yield from the last purification is 85.8%.

EXAMPLE 2

The procedure of Example 1 is followed, but using 3.8 mols (490.1 g) of N-ethyl-diisopropylamine. The yield in gabapentin form II, after purification by trituration in ethanol with 10% of water, is 75.8%.

EXAMPLE 3

The procedure of Example 1 is followed, but using an equivalent amount of tributylamine. The overall yield in gabapentin form II, after purification by trituration in ethanol with 10% of water, is 73.5%.

The invention claimed is:

1. A process for the preparation of pure gabapentin, in the crystalline form II, comprising starting from gabapentin hydrochloride, wherein said hydrochloride is dissolved in dry ethanol, the insoluble inorganic salts are filtered or centrifuged off, the ethanol solution free from the inorganic salts is added with a tertiary amine and a small amount of water, then cooled to 10–20° C., seeded with gabapentin form II, further cooled at +5 to −5° C. to precipitate gabapentin form II with a content of gabapentin III lower than 0.1% by weight and with a content in Cl⁻ ions not higher than 200–250 parts per million; and recovering said gabapentin form II.

2. The process as claimed in claim 1, wherein the weight/volume ratio of gabapentin hydrochloride to dry ethanol ranges from 1:6 to 1:9.

3. The process as claimed in claim 2, wherein said ratio ranges from 1:6.5 to 1:8.

4. The process as claimed in claim 1, wherein the tertiary amine is added in amounts of 1–1.25 mols per mole of hydrochloride.

5. The process as claimed in claim 4, wherein the tertiary amine is added in amounts of 1.1–1.2 mols per mole of hydrochloride.

6. The process as claimed in claim 1, wherein the tertiary amine is N-ethyl-diisopropylamine.

7. The process as claimed in claim 1, wherein the amount of water added to the ethanol solution free from the inorganic salts ranges from 7% to 10% by volume on the solution volume.

8. The process as claimed in claim 7, wherein the amount of water ranges from 8% to 9% by volume on the solution volume.

9. The process as claimed in claim 1, wherein the solution added with the tertiary amine and water is cooled to about 15° C., seeded with gabapentin form II and, after 4–8 hours at this temperature, is further cooled to about 0° C.

10. The process as claimed in claim 1, wherein the resulting gabapentin form II is further purified by suspension in approx. 10 parts by volume of ethanol containing about 10% by volume of water, heating for about 10–15 minutes at 35–45° C. and standing at room temperature overnight.

11. A process for the preparation of pure gabapentin, in the crystalline form II, starting from gabapentin hydrochloride, comprising dissolving said hydrochloride in dry ethanol, filtering or centrifuging off the insoluble inorganic salts; adding the ethanol solution to a tertiary amine and a small amount of water, cooling said solution, seeding said solution with gabapentin form II, further cooling said solution gabapentin II, and recovering the precipitated gabapentin form II, wherein said gabapentin II is recovered without a step of forming gabapentin III.

12. The process as claimed in claim 11, wherein the weight/volume ratio of gabapentin hydrochloride to dry ethanol ranges from 1:6 to 1:9.

13. The process as claimed in claim 12, wherein said ratio ranges from 1:6.5 to 1:8.

14. The process as claimed in claim 11, wherein the tertiary amine is added in amounts of 1–1.25 moles per mole of hydrochloride.

15. The process as claimed in claim 14, wherein the tertiary amine is added in amounts of 1.1–1.2 mols per mole of hydrochloride.

16. The process as claimed in claim 11, wherein the tertiary amine is N-ethyl-diisopropylamine.

17. The process as claimed in claim 11, wherein the amount of water added to the ethanol solution free from the inorganic salts ranges from 7% to 10% by volume on the solution volume.

18. The process as claimed in claim 11, wherein the solution added with the tertiary amine and water is cooled to 10–20° C., seeded with gabapentin form II and further cooled to +5 to −5° C.

19. The method according to claim 11, wherein said gabapentin II precipitate contains not more than 0.1% by weight of corresponding lactam, and 200–250 parts per million of Cl⁻ ions on average.

* * * * *